United States Patent
Eroume A Egom

(10) Patent No.: US 11,219,668 B2
(45) Date of Patent: Jan. 11, 2022

(54) METHOD OF TREATING A VASCULOPATHY IN A HUMAN SUBJECT

(71) Applicant: Emmanuel Eroume A Egom, Dartmouth (CA)

(72) Inventor: Emmanuel Eroume A Egom, Dartmouth (CA)

(*) Notice: Subject to any disclaimer, the term of this patent is extended or adjusted under 35 U.S.C. 154(b) by 822 days.

(21) Appl. No.: 15/530,196

(22) PCT Filed: May 1, 2015

(86) PCT No.: PCT/CA2015/000282
§ 371 (c)(1),
(2) Date: Dec. 12, 2016

(87) PCT Pub. No.: WO2015/192204
PCT Pub. Date: Dec. 23, 2015

(65) Prior Publication Data
US 2018/0318397 A1    Nov. 8, 2018

Related U.S. Application Data

(60) Provisional application No. 61/998,171, filed on Jun. 20, 2014.

(51) Int. Cl.
| | | |
|---|---|---|
| A61K 38/22 | (2006.01) | |
| A61K 38/17 | (2006.01) | |
| A61P 9/12 | (2006.01) | |
| C07K 14/58 | (2006.01) | |
| A61K 49/00 | (2006.01) | |

(52) U.S. Cl.
CPC ...... *A61K 38/2242* (2013.01); *A61K 38/1796* (2013.01); *A61K 49/0008* (2013.01); *A61P 9/12* (2018.01); *C07K 14/58* (2013.01); *G01N 2333/58* (2013.01)

(58) Field of Classification Search
None
See application file for complete search history.

(56) References Cited

U.S. PATENT DOCUMENTS

| | | |
|---|---|---|
| 8,741,861 B2 | 6/2014 | Mann |
| 2009/0035287 A1 | 2/2009 | Levine et al. |
| 2010/0204145 A1 | 9/2010 | Bevec |

FOREIGN PATENT DOCUMENTS

WO    WO2008046528    4/2008

OTHER PUBLICATIONS

Li et al., Natriuretic peptide receptor-C attenuates hypertension in spontaneously hypertensive rats. Hypertension, 63, 846-855, 2014. (Year: 2014).*
Rose et al., Natriuretic peptide C receptor signaling in the heart and vasculature. J. physiol., 586.2, 353-366, 2008. (Year: 2008).*
D'Alonzo GE, Barst RJ, Ayres SM, Bergofsky EH, Brundage BH, Detre KM, Fishman AP, Goldring RM, Groves BM, Kernis JT, et al. Survival in patients with primary pulmonary hypertension. Results from a national prospective registry. Ann Intern Med. Sep. 1, 1991;115(5):343-9.
Peacock AJ1, Murphy NF, McMurray JJ, Caballero L, Stewart S. An epidemiological study of pulmonary arterial hypertension. Eur Respir J. Jul. 2007;30(1):104-9.
Nogueira-Ferreira R. et al. Cellular interplay in pulmonary arterial hypertension: implications for new therapies. Biochim Biophys Acta. 1843, 885-893 (2014).
Simonneau G, Robbins IM, Beghetti M, Channick RN, Delcroix M, Denton CP, Elliott CG, Gaine SP, Gladwin MT, Jing ZC, Krowka MJ, Langleben D, Nakanishi N, Souza R. Updated clinical classification of pulmonary hypertension. J Am Coll Cardiol. Jun. 30, 2009;54(1 Suppl):S43-54. doi: 10.1016/j.jacc.2009.04.012.
Cogan JD, Pauciulo MW, Batchman AP, Prince MA, Robbins IM, Hedges LK, Stanton KC, Wheeler LA, Phillips JA 3rd, Loyd JE, Nichols WC. High frequency of BMPR2 exonic deletions/duplications in familial pulmonary arterial hypertension. Am J Respir Crit Care Med. Sep. 1, 2006;174(5):590-8.
Thomson JR, Machado RD, Pauciulo MW, Morgan NV, Humbert M, Elliott GC, Ward K, Yacoub M, Mikhail G, Rogers P, Newman J, Wheeler L, Higenbottam T, Gibbs JS, Egan J, Crozier A, Peacock A, Allcock R, Corris P, Loyd JE, Trembath RC, Nichols WC. Sporadic primary pulmonary hypertension is associated with germline mutations of the gene encoding. BMPR-II, a receptor member of the TGF-beta family. J Med Genet. Oct. 2000;37(10):741-5.
Casserly B, Klinger JR. Brain natriuretic peptide in pulmonary arterial hypertension: biomarker and potential therapeutic agent. Drug Des Devel Ther. Dec. 29, 2009;3:269-87.
Woodard GE, Rosado JA. Natriuretic peptides in vascular physiology and pathology. Int Rev Cell Mol Biol. 2008;268:59-93. doi: 10.1016/S1937-6448(08)00803-4.
Dijkgraaf I, Boerman OC. Radionuclide imaging of tumor angiogenesis. Cancer Biother Radiopharm. Dec. 2009;24(6):637-47. doi: 10.1089/cbr.2009.0694.
Maack T, Suzuki M, Almeida FA, Nussenzveig D, Scarborough RM, McEnroe GA, Lewicki JA. Physiological role of silent receptors of atrial natriuretic factor. Science. Oct. 30, 1987;238(4827):675-8.

(Continued)

*Primary Examiner* — Elly-Gerald Stoica
(74) *Attorney, Agent, or Firm* — Borden Ladner Gervais LLP; Kathleen E. Marsman

(57) ABSTRACT

The present invention is based upon the observation that inhibition of NPR-C Signaling pathway leads to the development of pulmonary arterial hypertension (PAH). Accordingly, the invention provides a mouse model for PAH, and proposes a method of using synthetic analogs of the NPR-C signaling pathway, specifically synthetic C-type atrial natriuretic factor or intermediates for, or modulators of, the NPR-C signaling pathway as anti-pulmonary vasculopathy agents. Activators of the NPR-C signaling pathway are disclosed to treat or prevent vasculopathy, including but not limited to PAH and other types of pulmonary hypertension, peripheral vascular disease, critical limb ischemia, coronary artery disease, and diabetic vasculopathy.

5 Claims, 10 Drawing Sheets

(56) References Cited

OTHER PUBLICATIONS

Suga S, Nakao K, Hosoda K, Mukoyama M, Ogawa Y, Shirakami G, Arai H, Saito Y, Kambayashi Y, Inouye K, et al. Receptor selectivity of natriuretic peptide family, atrial natriuretic peptide, brain natriuretic peptide, and C-type natriuretic peptide. Endocrinology. Jan. 1992;130(1):229-39.

Anand-Srivastava MB, Trachte GJ. Atrial natriuretic factor receptors and signal transduction mechanisms. Pharmacol Rev. Dec. 1993;45(4):455-97.

Levin ER, Gardner DG, Samson WK. Natriuretic peptides. N Engl J Med. Jul. 30, 1998;339(5):321-8.

Matsukawa N, Grzesik WJ, Takahashi N, Pandey KN, Pang S, Yamauchi M, Smithies O. The natriuretic peptide clearance receptor locally modulates the physiological effects of the natriuretic peptide system. Proc Natl Acad Sci U S A. Jun. 22, 1999;96(13):7403-8.

Jaubert J, Jaubert F, Martin N, Washburn LL, Lee BK, Eicher EM, Guénet JL. Three new allelic mouse mutations that cause skeletal overgrowth involve the natriuretic peptide receptor C gene (Npr3). Proc Natl Acad Sci U S A. Aug. 31, 1999;96(18):10278-83.

Palaparti A, Li Y, Anand-Srivastava MB. Inhibition of atrial natriuretic peptide (ANP) C receptor expression by antisense oligodeoxynucleotides in A10 vascular smooth-muscle cells is associated with attenuation of ANP-C-receptor-mediated inhibition of adenylyl cyclase. Biochem J. Mar. 1, 2000;346 Pt 2:313-20.

Pagano M, Anand-Srivastava MB. Cytoplasmic domain of natriuretic peptide receptor C constitutes Gi activator sequences that inhibit adenylyl cyclase activity. J Biol Chem. Jun. 22, 2001;276(25):22064-70.

Chauhan SD, Nilsson H, Ahluwalia A, Hobbs AJ. Release of C-type natriuretic peptide accounts for the biological activity of endothelium-derived hyperpolarizing factor. Proc Natl Acad Sci U S A. Feb. 4, 2003;100(3):1426-31.

Sun JZ, Chen SJ, Li G, Chen YF. Hypoxia reduces atrial natriuretic peptide clearance receptor gene expression in ANP knockout mice. Am J Physiol Lung Cell Mol Physiol. Sep. 2000;279(3):L511-9.

Itoh T, Nagaya N, Murakami S, Fujii T, Iwase T, Ishibashi-Ueda H, Yutani C, Yamagishi M, Kimura H, Kangawa K. C-type natriuretic peptide ameliorates monocrotaline-induced pulmonary hypertension in rats. Am J Respir Crit Care Med. Dec. 1, 2004;170(11):1204-11.

Hobbs A, Foster P, Prescott C, Scotland R, Ahluwalia A. Natriuretic peptide receptor-C regulates coronary blood flow and prevents myocardial ischemia/reperfusion injury: novel cardioprotective role for endothelium-derived C-type natriuretic peptide. Circulation. Sep. 7, 2004;110(10):1231-5.

Fagan KA, Tyler RC, Sato K, Fouty BW, Morris KG Jr, Huang PL, McMurtry IF, Rodman DM. Relative contributions of endothelial, inducible, and neuronal NOS to tone in the murine pulmonary circulation. Am J Physiol. Sep. 1999;277(3 Pt 1):L472-8.

Champion HC, Bivalacqua TJ, Greenberg SS, Giles TD, Hyman AL, Kadowitz PJ. Adenoviral gene transfer of endothelial nitric-oxide synthase (eNOS) partially restores normal pulmonary arterial pressure in eNOS-deficient mice. Proc Natl Acad Sci U S A. Oct. 1, 2002;99(20):13248-53.

\* cited by examiner

Parasternal short-axis echocardiographic view showing the characteristic flattening of the interventricular septum during diastole (A) and resumption of a normal circular left ventricle with the onset of systole (B)

Parasternal short-axis echocardiographic view at the midpapillary level showing the characteristic paradoxical ventricular septum motion in the NPRC -/- mice

A  NPRC +/+

B  NPRC -/-

Paradoxical ventricular septum motion

METHOD OF TREATING A VASCULOPATHY IN A HUMAN SUBJECT

FIELD OF THE INVENTION

The present invention relates to the human NPR-C signaling pathway and its role in the development of pulmonary hypertension (PH) and other disorders related to pulmonary vasculopathy including, but not limited to, pulmonary arterial hypertension (PAH). The invention further relates to methods of treating PH and disorders related to vasculopathy by administration of NPR-C signaling pathway activators.

BACKGROUND

Pulmonary arterial hypertension (PAH) is a progressive lung disorder which is characterized by sustained elevation of pulmonary artery pressure. Those patients with PAH typically have pulmonary artery pressure that is equal to or greater than 25 mm Hg with a pulmonary capillary or left atrial pressure equal to or less than 15 mm Hg. These pressures are typically measured in a subject at rest using right-heart catheterization. PAH, when untreated, leads to death (on average) within 2.8 years after being diagnosed. PAH is one of the five classes of pulmonary hypertension (PH). The other four types of PH are venous, hypoxic, thromboembolic and miscellaneous PH. PAH generally affects young and otherwise healthy individuals and strikes women twice as frequently as men. The average age of diagnosis has been estimated to be 36 years, with only 10% of patients over 60 years of age (DAlonzo et al, 1991; Peacock et al. 2007). Each year, between 15 and 50 people per million population are diagnosed with the disease, although this is certainly a low estimate (Peacock et al. 2007).

PAH is a condition in which the progressive obliteration of the pulmonary vasculature leads to increased resistance to blood flow through the lungs. In turn, this obstruction leads to increased stress on the right heart, which may develop into right heart failure and, ultimately, death. Although the "trigger" that leads to the disease is still unknown, a complex interplay among different types of cells occurs and multiple alterations have been verified: (i) intimal hyperplasia; (ii) medial hypertrophy and hyperplasia; (iii) adventitia proliferation; (iv) neointima formation and (v) occurrence of plexiform lesions. In addition, these changes are accompanied by vasoconstriction, local inflammation and in situ thrombi of the small pulmonary arteries and arterioles (Nogueira-Ferreira et al. 2014).

PAH patients can be sub categorized into three groups: those with Idiopathic PAH; those with Familial PAH; and those with Associated PAH—a form which is related to other conditions such as connective tissue diseases, among others. Idiopathic pulmonary arterial hypertension (IPAH) is the best described form of PAH and its pathophysiology may include loss of function mutations in the morphogenetic protein receptor 2 (BMP2) superfamily (J. Simonneau et al. 2009; Cogan et al. 2006). There are also heritable forms of the disease (HPAH), which have been often linked to the BMPR2 gene mutations (Thomson et al. 2000).

Standard therapies available on the market (e.g. prostacyclin analogs, endothelin receptor antagonists, phosphodiesterase inhibitors and soluble guanylate cyclases activators/stimulators) provide symptomatic relief and improve prognosis, but fall short as to re-establishment of structural and functional lung vascular integrity, as a basis for handicap-free long-term survival. The principles of these therapies are primarily hemodynamic, influencing vessel tone but having, as mentioned above, no proven direct influence on the pathogenic remodeling processes characteristic of this devastating disease, as most patients with PAH may already have full established pulmonary vascular remodelling at diagnosis. Moreover, by orders of magnitude more frequent, the unmet clinical need is even more pronounced in pulmonary vascular disorders outside the PAH group, e.g., those with underlying heart or lung disease and thromboembolic disease, for all of which no single medical treatment has been shown to improve outcome. In addition, the possibility of using these medicaments is restricted through the sometimes serious side effects and/or complicated types of administration.

Despite all the advances in the therapy of PAH there is as yet no prospect of cure of this deadly disease and the majority of patients continue to progress to right ventricular failure, albeit at a slower pace. Hence deciphering the molecular mechanisms which drive the maladaptive inward remodeling processes in PAH, as well as developing novel agents capable of preventing the progression or reversing pulmonary vascular remodelling, represents an important step in the treatment of patients with PAH and other subtypes.

Natriuretic peptides (NPs), including atrial (ANP), B-type (BNP), C-type (CNP) and dendroaspis (DNP) NPs constitute a family of at least four structurally-related hormones that may play a relevant role in cardiovascular homeostasis, including regulation of vascular tone, blood volume, endothelial permeability, and cardiac hypertrophy (Casserly et al. 2009; Woodard et al. 2008). Among the four family members, ANP and CNP have been demonstrated to suppress the signaling of vascular endothelial growth factor, a key regulator of PH (Dijkgraaf et al. 2009). The NPs exert their biological effects by binding to three specific receptors on the cell membrane denoted NPs receptors A, B and C (NPR-A, NPR-B and NPR-C) (Maack et al., 1987). Most attention has been given to NPR-A and NPR-B, which are well known particulate guanylyl cyclase (GC) receptors that mediate increases in cyclic guanosine monophosphate (cGMP) upon receptor activation. NPR-A (which binds ANP and BNP) and NPR-B (which binds CNP) increase intracellular cGMP levels following activation of a membrane bound GC enzyme (Suga et al. 1992). Most effects of NPs have been attributed to these receptors.

Conversely, much less is known about NPR-C, which is not directly coupled to GC signaling. NPR-C is known to bind ANP, BNP and CNP with similar affinity (Anand-Srivastava & Trachte, 1993). Furthermore, the affinity of NPR-C for the NPs is similar to the guanylyl cyclase-linked NPR-A and NPR-B receptors, suggesting that one class of receptor would not dominate the others on the basis of affinity for the peptides (Maack et al. 1987; Levin, 1993). Maack and colleagues demonstrated that the ring-deleted ANP analogue, $cANF_{4-23}$ (cANF), can compete for the vast majority of ANP binding sites in the isolated perfused rat kidney without altering guanylyl cyclase activity (Maack et al. 1987). In this study the specific binding of radiolabelled ANP was almost completely inhibited by cANF ($10^{-7}$ m) demonstrating that cANF can occupy up to 99% of ANP binding sites. Despite its inability to stimulate guanylyl cyclase activity, cANF significantly increased sodium excretion and decreased blood pressure in conscious rats. These effects were attributed to a significant increase in plasma ANP levels in the presence of cANF (Maack et al. 1987). It was further concluded that the ability of ANP to bind NPR-C was occluded by cANF and that the majority of renal ANP receptors were 'silent.' This appears to be the basis for the classification of NPR-C as a 'clearance receptor.'

Accordingly, it was suggested that the main function of NPR-C is to remove NPs from the circulation, thereby buffering the levels of NP available to alter guanylyl cyclase activity and intracellular cGMP levels via NPR-A and NPR-B. This hypothesis received further support from data derived from a transgenic mouse model in which NPR-C was genetically ablated (Matsukawa et al. 1999). The animals have a moderately but statistically significantly lowered blood pressure and with age show an increase in daily water uptake with a significant increase in urinary output. The NPR-C$^{(-/-)}$ mice also have a defect in the ability to concentrate their urine. The observed alterations in renal function were interpreted as being the result of a failure of local clearance of NPs in the glomerular and post-glomerular structures resulting in an increase in filtered volume and a decrease in water reabsorption. The decrease in blood pressure was attributed to simple hypovolemia. These experiments also showed that the half-life of radiolabelled ANP in the circulation of homozygote mice lacking NPR-C was 66% longer than in wild-type animals and it was concluded that NPR-C functioned mainly as a modulator of NP availability at target organs. Unexpectedly, the authors also found that mice lacking NPR-C exhibit striking skeletal abnormalities, including hunched backs, dome-shaped skulls, elongated tails, increased body length, decreased weight, elongated femurs, tibias, metatarsal, and digital bones as well as a more constricted thoracic cages than their counterpart wild type. However, the authors did not perform any evaluation of the heart nor did they make any examination of the pulmonary vasculature.

Several spontaneously occurring mutants in the NPR3 gene have been identified, the first of which was called longjohn (lgj) due to the skeletal defects described above. A French group studied them to examine and compare the skeletal defects among the three strains (Jaubert et al., 1999). Again, the authors did not perform any evaluation of the heart nor did they make any examination of the pulmonary vasculature.

US20040898490 patent disclosed a method of using synthetic analogs of NPs as pro-lipolytic, as anti-obesity agents. Again, the inventors did not perform any evaluation of the heart nor did they make any examination of the pulmonary vasculature.

Existing literature has disclosed the potential involvement of NPR-C in several disease processes via its clearance role. These effects have been largely attributed to NPR-A and NPR-B (and subsequent changes in cGMP signaling). Although still commonly called a clearance receptor (and thus largely ignored), recent evidence suggests that NPR-C has other biological activity other than simply NPs clearance. Several groups have shown that NPR-C is coupled to a pertussis toxin sensitive inhibitory G protein (G) and mediates a reduction in adenylyl cyclase (AC) activity and intracellular cAMP levels (Palaparti, et al. 2000; Pagano et al. 2001). Recently, it has been postulated that the vasodilatory effects of endothelium-derived hyperpolarizing factor may be attributed to such NPR-C mediated adenylyl cyclase inhibition (Chauhan et al. 2003).

Several basic and clinical research projects have been carried out to understand the roles of NPs in regulating pulmonary vascular tone and remodeling, as well as their roles in the pathogenesis of hypoxia or monocrotaline-induced PH. All the antimitogenic, antifibrotic, and antihypertrophic effects of NPs on pulmonary vascular remodeling and maladaptive hypertrophic responses in the right ventricle were reported to be linked to the GC-linked NPs' receptors. Even the often observed down regulation of NPR-C in hypoxia-associated PH was repeatedly reported to be part of a compensatory mechanism of the lungs aimed at reducing NPs clearance from the circulation, thus enhancing the biological effects of NPs and mitigating the severity of hypoxia-induced PH (Sun et al. 2000; Casserly et al. 2009; Itoh et al. 2004) Again, the intrinsic impaired NPR-C signaling pathway as the underlying cause of PH has never been taught, suggested or implied in the literature.

In summary, there has been no suggestion in the art that NPR-C signaling pathway would be useful in any therapeutic manner as a treatment for PH. Attempts to define the new and direct role of the intrinsic NPR-C signaling pathway in PAH may be aided by the use of cANF as a specific and selective agonist of NPR-C.

SUMMARY OF THE INVENTION

The present invention relates to the activation of NPR-C signaling pathway and thereby inhibiting the associated development of PH and other disorders related to pulmonary vasculopathy.

Other embodiments of the present invention are directed to the use of synthetic analogs of NPR-C signaling pathway, specifically the synthetic C-type atrial natriuretic factor (cANF), or intermediates for or modulators of NPR-C pathway as anti-pulmonary hypertension or anti-pulmonary vasculopathy agents.

The use of activators to NPR-C signaling pathway is also disclosed to treat or prevent vasculopathy, including, but not limited to, PAH and other types of PH, peripheral vascular disease, critical limb ischemia, coronary artery disease, and diabetic vasculopathy. Another embodiment is a method of characterizing a vasculopathy, using a subject having a polymorphism that results in the loss of function in the gene encoding NPR-C.

A third embodiment of the invention is to provide a transgenic animal model for examining the effects of a candidate agent (e.g., a small molecule drug or an endogenous factor) on a phenomenon associated with PH. Such transgenic animal models are useful for screening candidate agents for use in treating or relieving the symptoms of PH.

DETAILED DESCRIPTION OF THE INVENTION

Definitions

Figure 1:
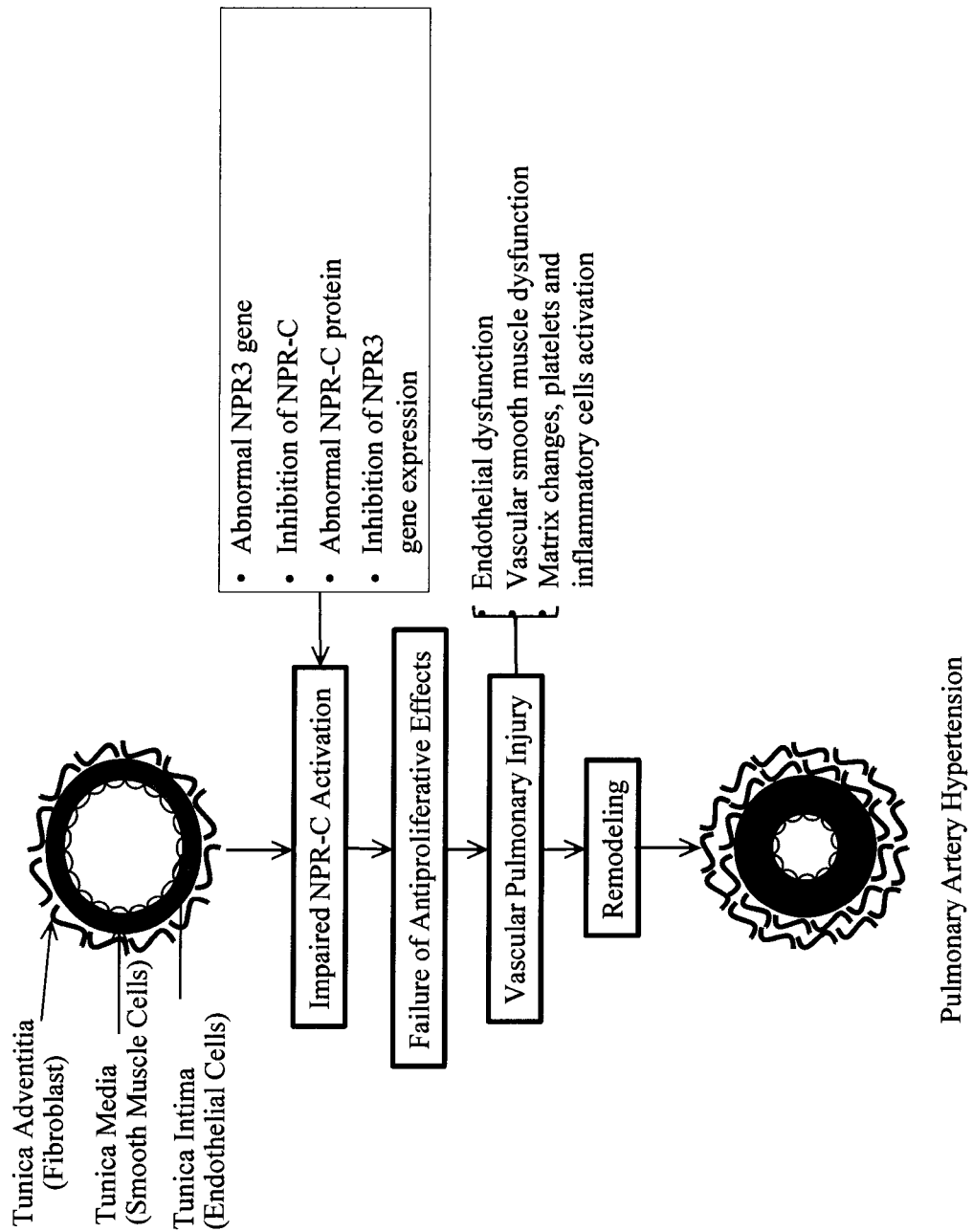
FIG. 1 illustrates a schematic representation of a cascade of events following an impairment of NPR-C signaling pathway. The impaired NPR-C signaling pathway may be the result of several factors, including but not limited to an abnormal NPR3 gene, an inhibition of NPR3 gene expression, or an inhibition or abnormal NPR-C protein. Impaired activation of this signaling pathway leads to failure of the antiproliferative effect of NPR-C in the pulmonary vasculature, which in turn results in vascular pulmonary injury, including endothelial dysfunction, vascular smooth muscle dysfunction, matrix changes, and platelets, as well as inflammatory cell activation. The proliferation of smooth muscle in pulmonary arterioles, secondary to remodelling, would then ultimately lead to PAH.

As used herein, "a" or "an" means "one or more."

Unless specifically defined otherwise, all technical and scientific terms used herein shall be taken to have the same meaning as commonly understood by one of ordinary skill in the art (e.g., in cell biology, cell culture, molecular genetics, immunology, immunohistochemistry, protein chemistry, and biochemistry).

As used herein, the term "subject" (also referred to herein as a "patient") includes warm-blooded animals, preferably mammals, including mice, rats, rabbits, pigs, sheep, goats, cattle, and other domestic farm animals, zoo animals, as well as higher primates and humans.

As used herein, the term "vasculopathy" includes, but is not limited to, pulmonary vasculopathy, PAH and other types of PH, peripheral vascular disease, critical limb ischemia, coronary artery disease, and diabetic vasculopathy.

As used herein the terms "treating", "treat" or "treatment" refer to obtaining a desired physiological or pharmacological effect that may be partially or completely effective in preventing a disease, or may be partially or completely effective in preventing, reducing, or improving one or more symptoms of, or other adverse effects caused by, a disease. The desired physiological or pharmacological effect may be achieved by administering a therapeutically effective amount of an NPR-C signalling pathway activator as defined herein, wherein said amount of activator is sufficient to reduce or eliminate at least one symptom of vasculopathy.

As used herein, an "effective amount" is an amount that achieves the stated goal, which may be treatment and/or prevention of vasculopathy, or any symptom associated with vasculopathy. It is contemplated that in the context of treatment an effective amount produces a therapeutic benefit, which includes, but may not be necessarily limited to the following characteristics with respect to pulmonary arterial hypertension: reducing mean pulmonary pressure, increasing cardiac output/cardiac index measured by either thermodilution or Fick, improving timed walk distance (e.g., six-minute walk), improving metabolic equivalents (MET) {e.g., exercise treadmill test), reducing anginal pain frequency, reducing dyspnea, synocope, presyncope, symptoms of right heart failure including edema and ascites, preventing need for lung or heart transplant, reducing length of stay in intensive care, reducing length of stay in hospital, or prolonging life.

As used herein, the terms "comprises," "comprising," "containing" and "having" and the like are open-ended as defined by U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

This application is directed to the surprising and unexpected discovery that NPR-C knockout (NPR-C$^{(-/-)}$) mice are PAH-prone and, therefore, represent an experimental animal model for PAH. The NPR-C$^{(-/-)}$ mice show similar pathology when compared to human PAH patients, including right atrial dilation, tricuspid regurgitation as well as echocardiographic signs of right ventricular pressure overload, including paradoxical bulging of the septum into the left ventricle during systole, and hypertrophy of the right ventricular free wall and trabeculae. The left ventricular systolic and diastolic function are within normal limits in NPR-C$^{(-/-)}$ mice. Doppler echocardiography assessment reveals a higher right ventricular systolic pressure (RVSP) and thus a higher pulmonary artery systolic pressure (PASP) in NPR-C$^{(-/-)}$ mice compared with wild-type littermates. This significant increase in RVSP and PASP in NPR-C$^{(-/-)}$ mice was confirmed with right heart catheterization. Accordingly, the invention is directed to the use of the NPR-C$^{(-/-)}$ mouse as a model system for PAH.

The mouse model of the present invention may be used in a wide variety of assays of screening agents for their potential effect on a patient with PAH. In this embodiment, the agent is administered to the mouse and the effect on the mouse is evaluated. For example, the model can be used to evaluate, i.e., screen, potential therapeutic agents for preventing or treating conditions associated with PAH.

In addition, the invention pertains to the use of NPR3 gene polymorphism for diagnosis of vasculopathy. The invention is based on the discovery that loss of function or mutations of NPR3 gene, particularly loss of function or mutations of the gene encoding NPR-C play a role in the development of PAH. Likewise, mutants of the NPR-C protein, as well as related derivatives, fragments and homologs thereof, and NPR-C nucleic acids encoding them, may also have a role in the development of PAH.

The invention provides a method for the use of one or more activators of the NPR-C signaling pathway for the treatment and prevention of PH and disorders related to vasculopathy, comprising administering to the subject a therapeutically effective amount of said activator. These compounds and compositions may be administered to humans in a manner similar to other therapeutic agents. Therapeutics of the invention may be administered either alone or in combination with other therapies, e.g., therapeutics effective against PAH and PH. Other therapeutic agents that have been used to treat PAH include, but are not limited to, the following: anticoagulants (such as Coumadin or Warfarin), calcium channel blockers (such as amlodipine, diltiazem, nifedipine, felodipine, isradipine, nicardipine, or verapamil), prostacyclins (such as epoprostenol, treprostinil, iloprost), nitric oxide (only used in acute settings), soluble GC stimulators and activators (riociguat), diuretics, cardiac glycosides (digoxin), endothelin antagonists (including nonselective inhibition with bosentan), phosphodiesterase inhibitors (such as sildenafil), endopeptidase inhibitors, lipid lowering agents, thromboxane inhibitors (such as terbogrel), or oxygen.

The invention further provides a method for acute administration of a therapeutically effective amount of cANF to the subject suffering from PH or other disorders related to vasculopathy, in order to significantly reduce RVSP and PASP without alteration of the systemic arterial pressure. The magnitude of this reduction may be greater in subjects with concomitant diabetes or coronary artery disease, including heart failure, who may have endothelial dysfunction. This observation is supported by the finding that, in the coronary vasculature, the vasorelaxant effect of the NPR-C pathway may be increased in the presence of nitric oxide (NO) synthase inhibition (Hobbs et al. (2004)). This observation supports synergistic and complementary functions for NPR-C pathway and NO-mediated signaling. The inhibition of one pathway may thus be compensated for by the upregulation of the other. This may be of particular clinical significance in patients with PAH who are known to have endothelial dysfunction and thus reduced or loss of NO pathway (Fagan et al. 1999; Champion et al. 2002).

The precise nature of the role of NPR-C signaling pathway in pulmonary vascuolopathy is not yet fully elucidated. Evidence suggests that chronic hypoxia causes a significant down regulation of NPR-C expression in several tissues, including pulmonary vascular smooth muscle, independently of changes in NPs levels and expression of other NPs' receptors (Sun et al. 2000). This down regulation of NPR-C expression and associated impaired NPR-C pathways may lead to failure of the antiproliferative effect in the pulmonary vasculature, which would then ultimately lead to PAH (FIG. 1). Therefore, an impaired NPR-C pathway is a common underlying cause of all hypoxia-associated vasculopathy, including, but not limited to, pulmonary vasculopathy and chronic thromboembolic pulmonary hypertension (CTEPH). The most common causes of PH are chronic lung and left sided heart disease. The development of PH in these conditions occurs, at least partially, as the result of chronic hypoxia. This observation suggests that NPR-C pathway represents, therefore, a therapeutic target to inhibit pulmonary vascular remodeling and maladaptive increases in pulmonary arterial pressures in patients with heart failure or CTEPH.

Figure 2:
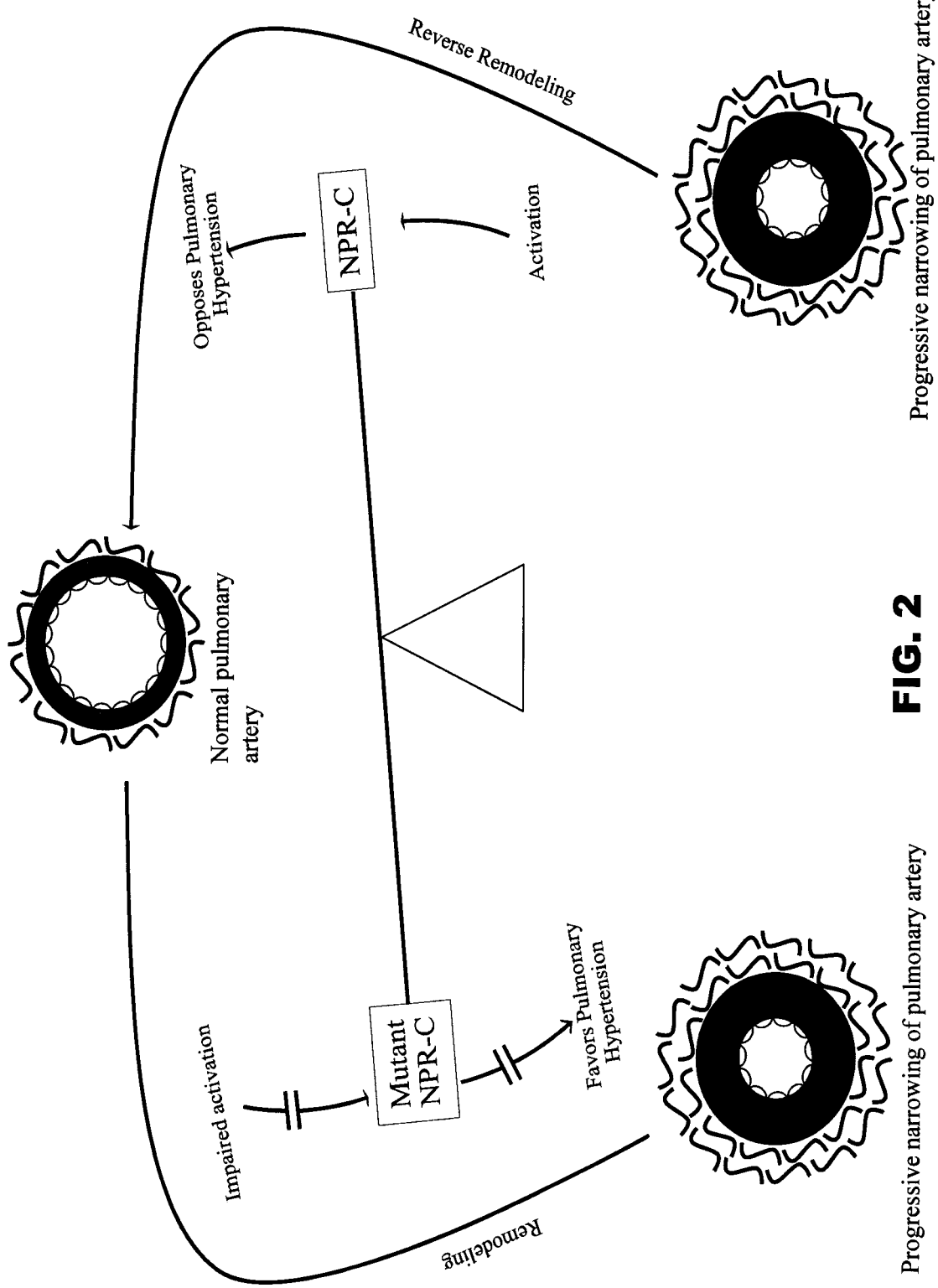
FIG. 2 illustrates the loss of homeostasis with NPR-C signaling pathway. The imbalance between impaired activation and physiological activation may cause or prevent the development of PAH. Impaired activation of NPR-C signaling pathway leads to failure of the antiproliferative effect of NPR-C in the pulmonary vasculature, which in turn results in PAH. Activators to NPR-C pathway initiate signaling that results in the inhibition of cell proliferation in pulmonary artery smooth muscle cells and therefore reverses the remodelling that is typical to PAH.
Figure 3:
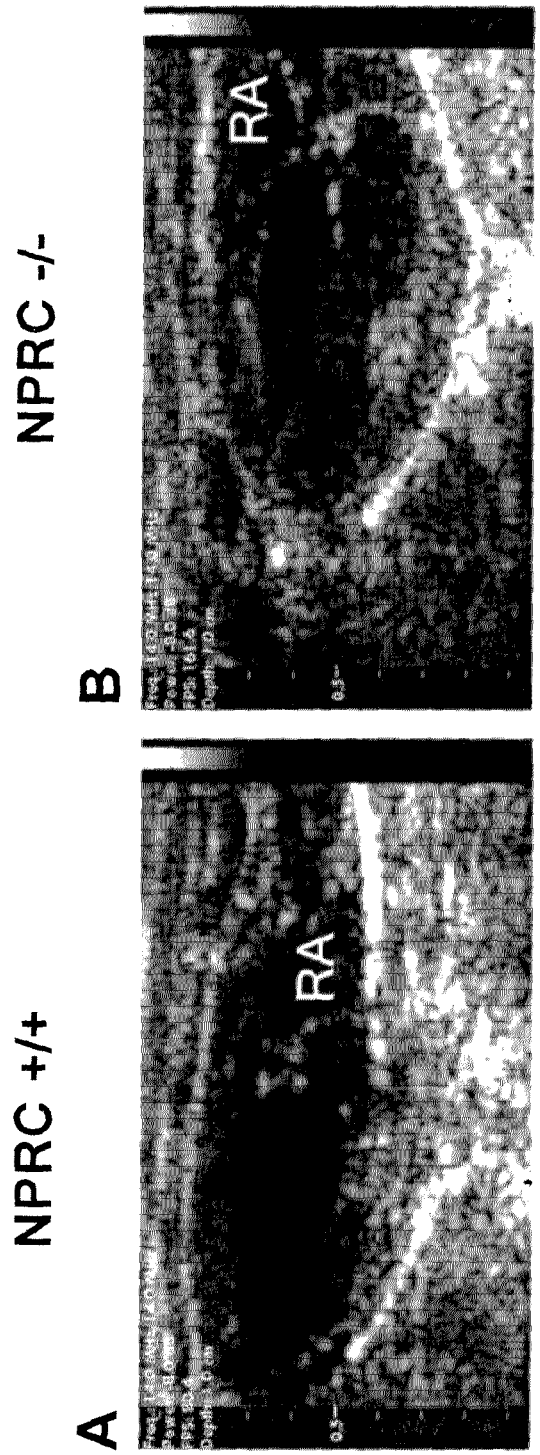
FIGS. 3a and 3b illustrate the results of apical four-chamber echocardiography in NPRC$^{+/+}$ and NPRC$^{-/-}$ mice and illustrates right atrial dilation as evidenced by the RA notation on the respective figures.
Figure 4:
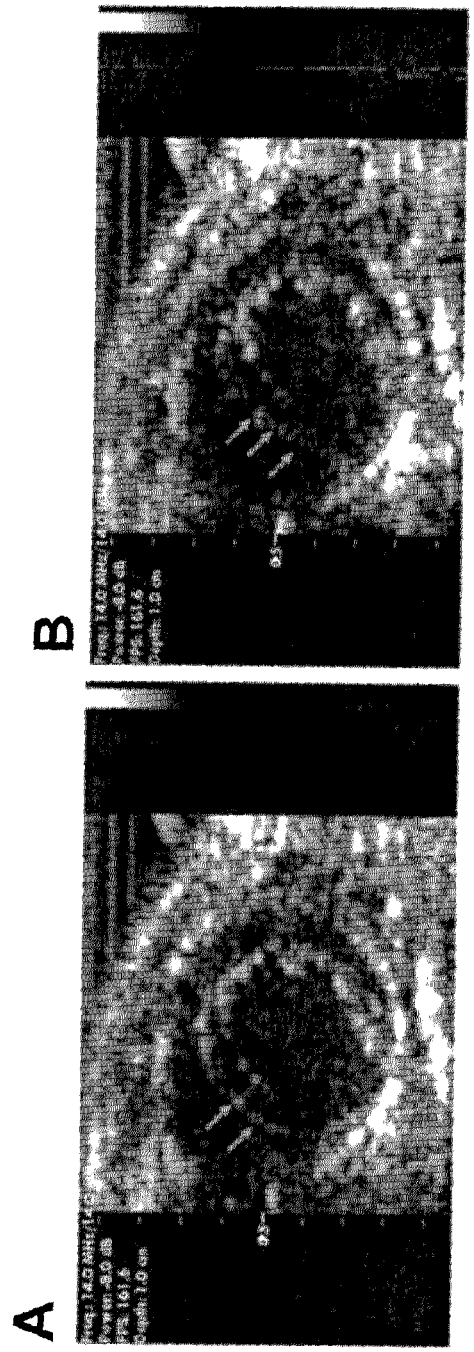
FIGS. 4a and 4b show a 2D view of the parasternal short-axis echocardiographic view at the mid papillary level showing the paradoxical ventricular septum motion including flattening and bulging into the left ventricle during systole in the NPRC$^{-/-}$ mice.
Figure 5:
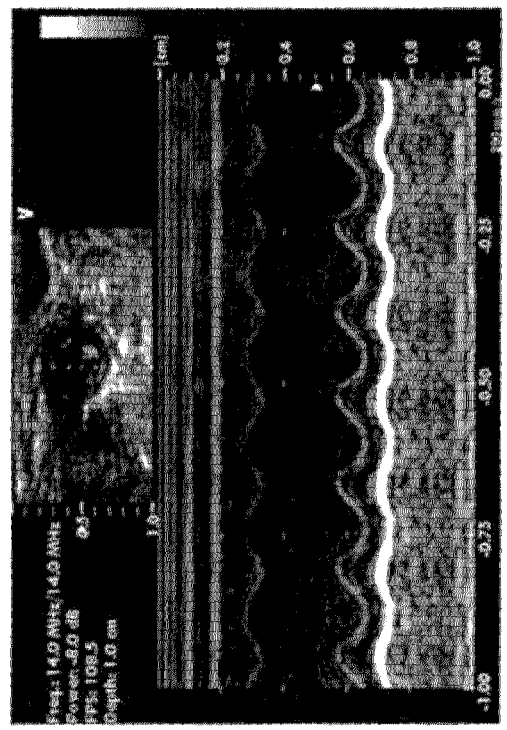
FIGS. 5a and 5b show an M-Mode view of the parasternal short-axis echocardiographic view at the mid papillary level showing the paradoxical ventricular septum motion including flattening and bulging into the left ventricle during systole in the NPRC$^{-/-}$ mice.
Figure 5:
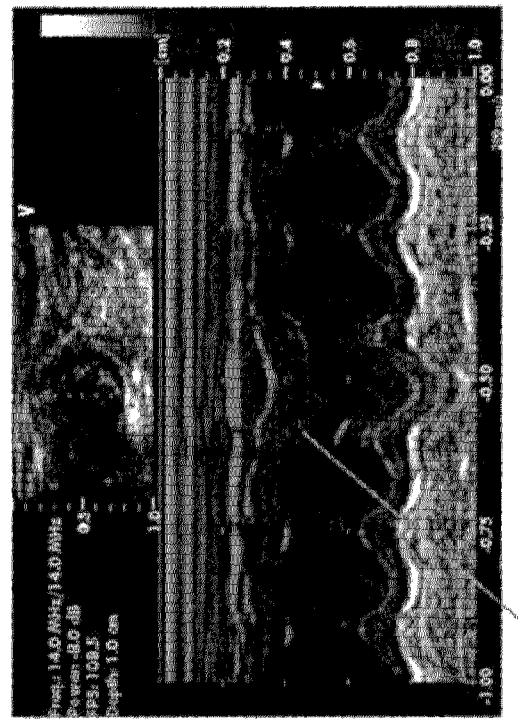
Figure 5:
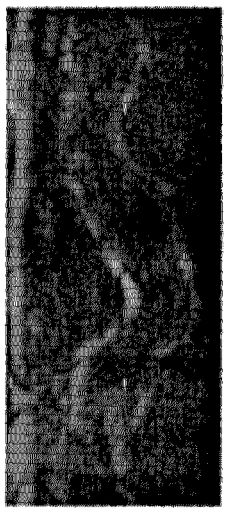

It is hypothesized that the NPR-C pathway may prevent cellular proliferation in some types of cells, with the result that abnormal NPR-C pathway activity may permit excess cell growth and proliferation in response to a variety of injuries. The proliferation of smooth muscle in pulmonary arterioles would then ultimately lead to PAH. These affirmations are supported by the proposed observation that transgenic mice with genetic deletion of NPR-C exhibit PAH. Therefore, the fundamental mechanism of NPR-C-related PAH may be an imbalance of growth signaling caused, at least partially, by an impaired or reduction in the braking function of NPR-C. (FIGS. 1 and 2). In summary, an abnormal NPR-C pathway plays an important role in the pathogenesis of PAH and in particular IPAH, and is likely causally linked to some cases in familial PAH (FPAH) and a substantial percentage of IPAH patients.

Although the foregoing description refers to particular embodiments, it will be understood by one of skill in the art that the present invention is not limited to the disclosed embodiments. Those of ordinary skill in the art will recognize that various modifications may be made to the disclosed embodiments and that such modifications are intended to be within the scope of the present invention.

EXAMPLES

Statistical Analysis

All data are presented as means±SEM. Data were analyzed using Student's t-test. $P<0.05$ was considered significant.

Example 1: Echocardiography

A study was conducted to examine the differences in cardiac structure and function in NPR-C$^{+/+}$ (wild type) and age matched, littermate NPR-C$^{-/-}$ mice by echocardiography. Two-dimensional, Doppler echocardiography measurements and quantification were performed according to recommendations of the European Society of Echocardiography.

Wild type (n=10) and NPRC$^{-/-}$ (n=10) mice were scanned at 12 months. Mice were placed in an induction chamber with constant inflow of 5% isoflurane mixed with 100% oxygen. Once each mouse was asleep, it was removed from the induction chamber, weighed and placed on a heating platform with electrocardiogram contact pads. The mouse's nose was placed into a nose cone providing a flow of 1-2% isoflurane in 100% oxygen. Excess gases were evacuated passively using an activated charcoal absorption filter. The eyes were covered with a petroleum based ophthalmic ointment. Electrode gel was placed on the paws and the paws were taped over the electrocardiogram contact pads on the heating platform. A rectal probe was lubricated with gel, placed in the rectum and taped to the platform. The temperature was maintained at 36.5 to 37.5° C. Depilatory cream was applied to the chest of the mouse and removed after two minutes. Ultrasound gel was placed on the chest of the anesthetized mouse. The ultrasound probe was placed in contact with the ultrasound gel and scanning was performed over 20 minutes. B-mode, M-mode and spectral Doppler images were obtained. The temperature and heart rate (HR) were constantly monitored during the scanning. Once completed, all probes and monitors were removed from the mouse. The mouse was cleaned with water and allowed to recover on the heated platform. Once awake, the mouse was returned to its cage.

Estimation of RVSP by Doppler Echocardiography assessment of tricuspid valve regurgitation (TR) jet peak velocity accurately predicts the pulmonary artery systolic pressure (PASP) observed by invasive measurement. TR was graded as none, trace, mild, moderate, or severe by assessment of the colour-flow jet in relation to the right atrium (RA) area in apical 4 chamber view. With pulse-wave Doppler, the maximum peak TR velocity (V) recorded from any view was used to determine the RVSP with the simplified Bernoulli equation (RVSP=4V2+RAP), with RA pressure (RAP) obtained via right heart catheterization. PASP equates to RVSP in the absence of pulmonic stenosis and RV outflow tract obstruction, as was the case in this study. Other calculations were performed using echocardiographic derived values. Percent shortening fraction was calculated from M-mode measurements using the leading edge to leading edge method via the formula % Shortening Fraction (% SF)=left ventricular internal diameter (diastole) [LVID (d)]−left ventricular internal diameter (systole) [LVID(s)]/LVID(d).

As illustrated in FIGS. 3a and 3b, 4a and 4b, and 5a and 5b, the NPR-$C^{(-/-)}$ mice had right atrial dilation and echocardiographic signs of right ventricular pressure overload, including flattening and paradoxical bulging of the septum into the left ventricle during systole, and hypertrophy of the right ventricular free wall and trabeculae. Similar testing (figures not shown) indicated a severe tricuspid regurgitation jet in the NPRC$^{-/-}$ mice. All these findings are also typically seen in human patients with PAH. The ejection fraction (EF) (69±2.4 in NPR-$C^{+/+}$ vs. 74 W 2 in NPR-$C^{(-/-)}$, p=0.11) and fractional shortening (FS) (34±4.3 in NPR-$C^{+/+}$ vs. 38.3±3.8, P=0.13) tended to be greater in NPR-$C^{-/-}$ mice, although these did not reach statistical significance as would be expected in the human patient with PAH. Severe TR was detected in all NPR-C(−/−) mice while most NPR-C(+/+) mice had none or trace TR. Consistently, Doppler echocardiography assessment revealed a higher RVSP and thus a higher PASP compared with wild-type littermates (25±1 mmHg vs 7±1 mmHg, P<0.001).

Example 2: Right Heart Catheterization and Administration of cANF

To confirm the presence of increased pulmonary artery systolic pressure among NPR-$C^{-/-}$ mice, right heart catheterization was performed in both NPR-$C^{+/+}$ (wild type) and age matched, littermate NPR-$C^{-/-}$ mice.

Mice were placed in an induction chamber with constant inflow of 5% isoflurane mixed with 100% oxygen. Once each mouse was asleep, it was removed from the induction chamber, weighed and placed on a heated surgical table and secured with surgical tape. The mouse's nose was placed into a nose cone with a flow of 3% isoflurane in 100% oxygen. The animals were then shaved to expose the surgical area. An incision of ~1 inch length was made, extending from the animal's chin down to the right armpit. The thyroid gland was then blunt-dissected upward to expose the underlying tissue and the right jugular vein. The jugular vein was then separated from surrounding tissue using dissecting forceps until the body of the vessel was completely free from adherent tissues. The cranial end of the jugular was tied off completely, and a loose tie was then made at the caudal end of the exposed jugular using 4-0 braided silk suture. Four-inch microdissecting scissors were then used to make a small incision in the medial aspect of the right jugular vein. A Millar 1.4 French pressure-volume microtip catheter transducer connected to a PowerLab/8s (AD Instruments) was then inserted through the incision and gently threaded down into the right ventricle. Proper placement within the ventricle was determined through observation of the pressure-volume loop obtained from the catheter. The loose caudal suture was then tightened to secure the catheter in place. Once the catheter was properly placed, data including HR and the right ventricular systolic pressure (RVSP) were recorded and analyzed using a data acquisition system (Chart, AD Instruments).

Figure 6:
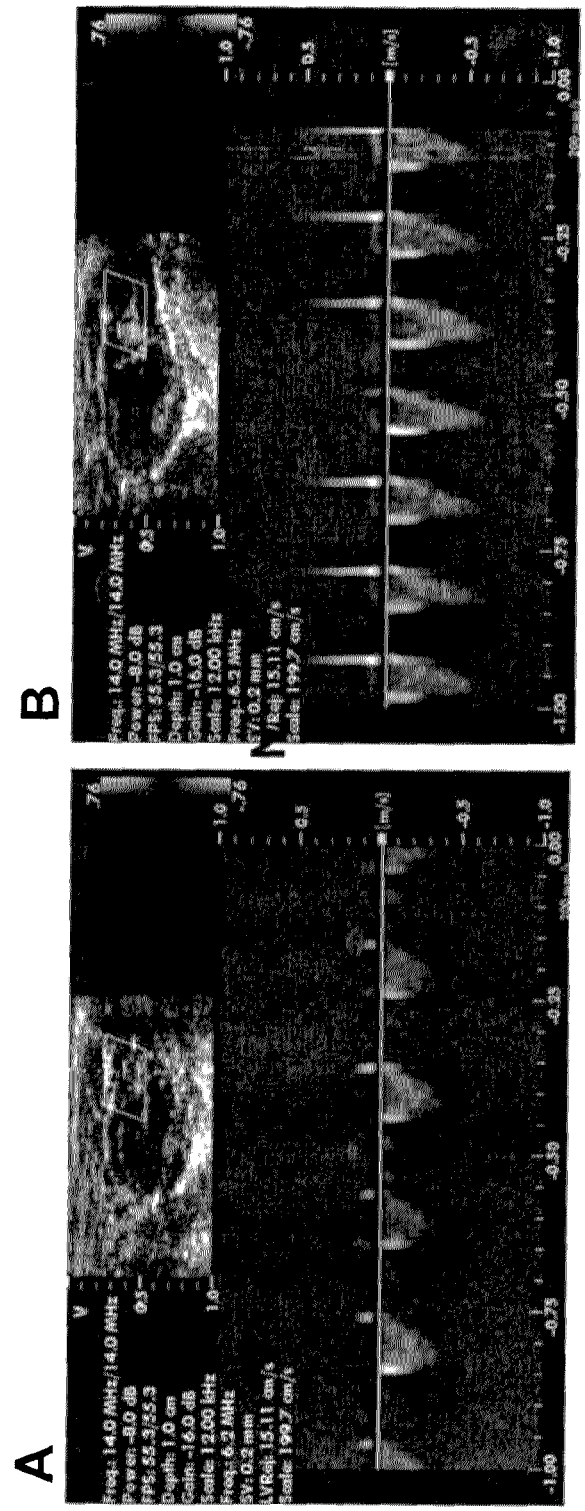
FIG. 6 demonstrates the estimation of RVSP/PASP by using the maximum velocity of the tricuspid regurgitation jet, and reveals a higher RVSP/PASP in the NPRC$^{-/-}$ mice.
Figure 7:
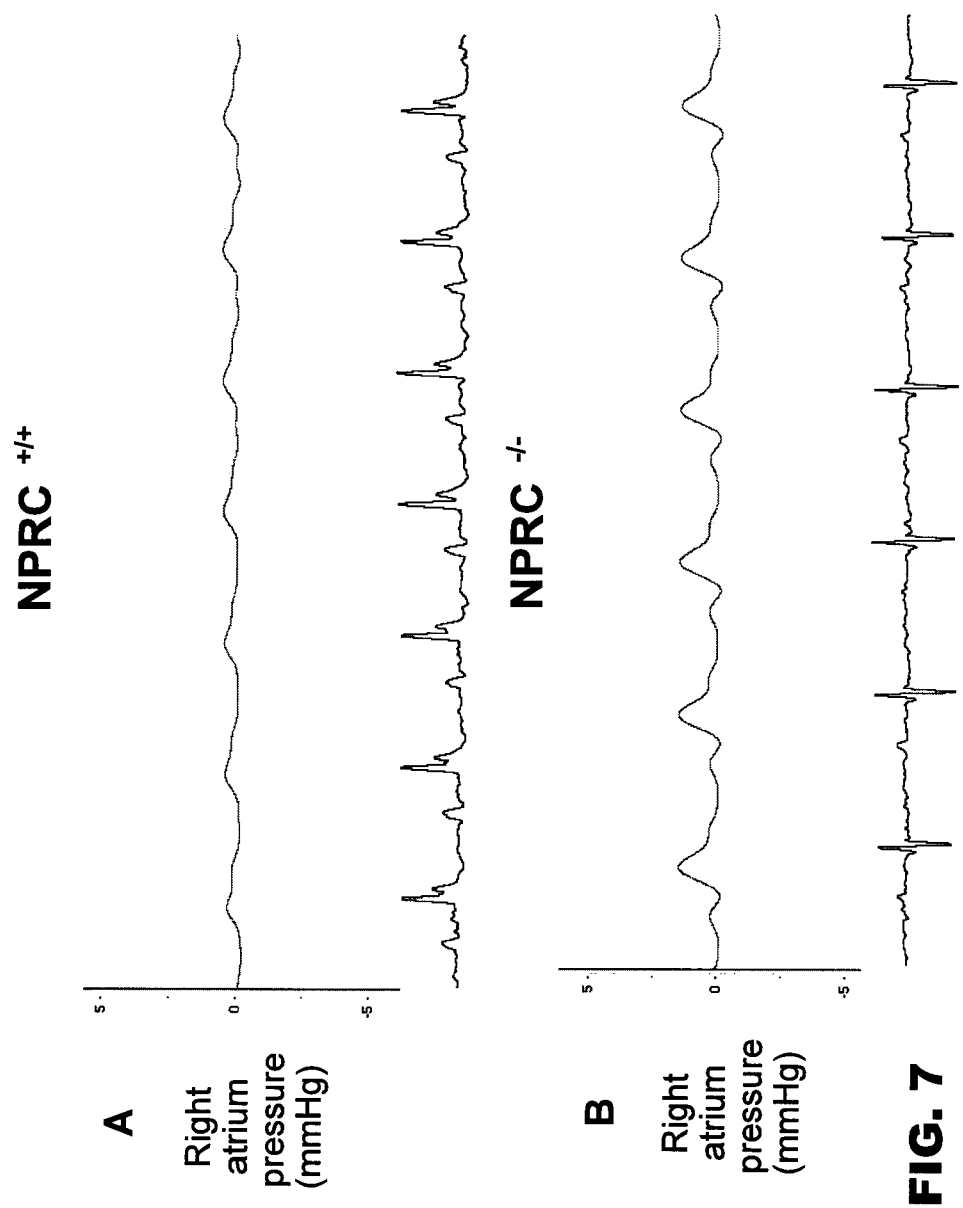
FIGS. 7a and 7b show representative examples of the right atrium pressure tracings in the NPRC$^{+/+}$ and NPRC$^{-/-}$ mice, demonstrating the presence of an increased atrial pressure in the NPRC$^{-/-}$ mice.
Figure 8:
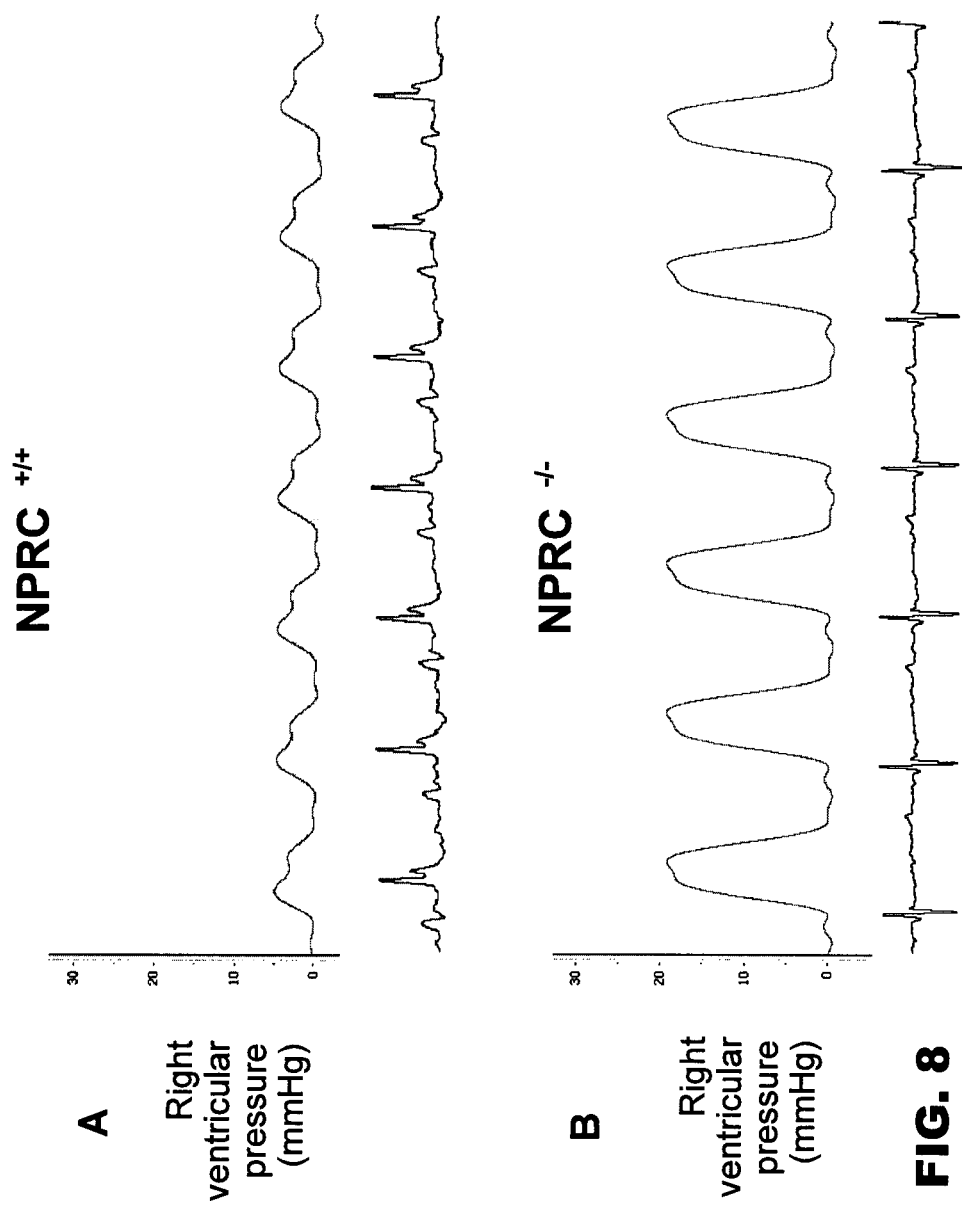
FIGS. 8a and 8b show representative examples of right ventricular pressure tracings in the NPRC$^{+/+}$ and NPRC$^{-/-}$ mice, demonstrating the presence of an increased right ventricular systolic pressure (RVSP) in the NPRC$^{-/-}$ mice.

As illustrated in FIGS. 6a and 6b, right atrial pressure was significantly elevated in the NPR-$C^{-/-}$ mice compared to their age matched, littermate NPR-$C^{+/+}$ mice, at baseline (1.99±0.08 mm Hg vs 0.38±0.02 mm Hg, respectively (P=0.01)). As illustrated in FIGS. 7a and 7b, right ventricular systolic pressure (RVSP) was significantly elevated in NPR-$C^{-/-}$ mice compared to their age matched, littermate NPR-$C^{+/+}$ mice, at baseline (21.95±0.56 mmHg vs 5.3±0.6 mmHg, respectively (P<0.001)).

Each NPR-$C^{+/+}$ mouse was administered a dose of the NPRC receptor agonist, cANF, by means of an intraperitoneal (IP) bolus of 1 µL of cANF (50 nM) in 15 mL of distilled water. Consistently, the administration of the cANF in NPR-$C^{+/+}$ mice, decreased the RVSP and therefore PASP by 50%, and HR by 11%, but had no effect on blood pressure. PASP equates to RVSP in the absence of pulmonic stenosis and RV outflow tract obstruction, as was the case in this study.

Figure 9:
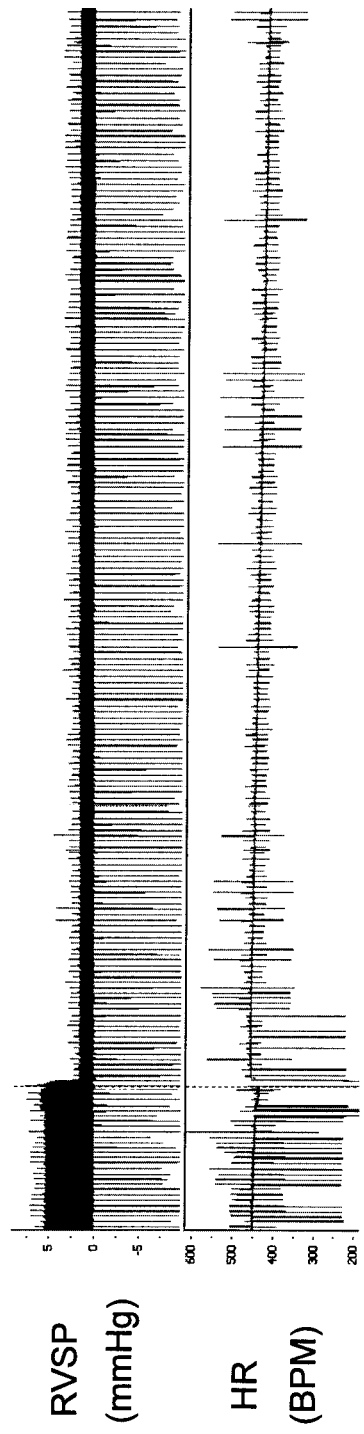
FIG. 9 demonstrates the effect of cANF administration on the right ventricular systolic pressure and heart rate in a diabetic mouse.
Figure 10:
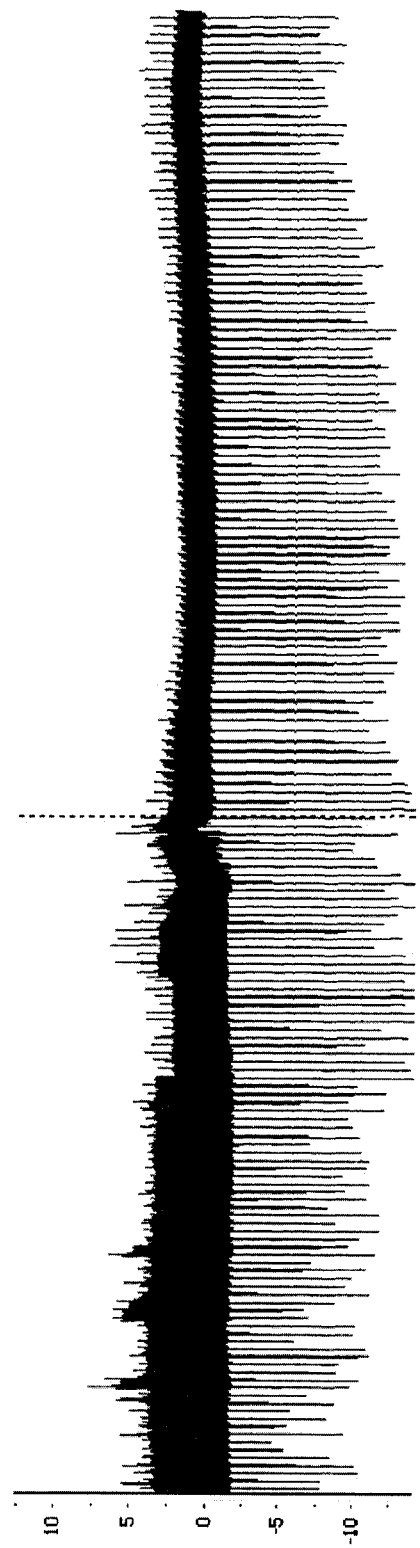
FIG. 10 demonstrates the effect of cANF administration on the right ventricular systolic pressure in NPR-C$^{+/+}$ mice. cANF significantly reduces RVSP.

Interestingly, the effect on RVSP and therefore PASP was more striking in the age matched diabetic mice (more than 75% reduction in RVSP) as illustrated in FIG. 9. The increased magnitude of this reduction may be due to the concomitant endothelial dysfunction in diabetic mice, and a similar response is anticipated in subjects with concomitant coronary artery disease including heart failure, which may also have endothelial dysfunction.

What is claimed is:

1. A method of treating or preventing a vasculopathy in a subject, the method comprising: administering to the subject a therapeutically effective amount of an activator of NPR-C signaling, wherein the activator binds the NPR-C and reduces intercardiac and/or pulmonary pressure, wherein the subject is a human subject and wherein the activator of NPR-C signaling is cANF or a functional analog thereof.

2. The method of claim 1, wherein said vasculopathy comprises pulmonary arterial hypertension (PAH).

3. The method of claim 1, wherein said vasculopathy comprises pulmonary hypertension (PH).

4. The method of claim 3, wherein said pulmonary hypertension is a complication of a medical condition selected from the group consisting of: left sided heart disease, heart failure, chronic hypoxia and thromboembolic disease.

5. The method of claim 1, wherein the activator of NPR-C signaling is cANF.

\* \* \* \* \*